United States Patent [19]

Stevens et al.

[11] Patent Number: 5,780,294
[45] Date of Patent: Jul. 14, 1998

[54] CULTURE VESSEL ASSEMBLY

[75] Inventors: Timothy A. Stevens, Warwick, N.Y.;
Tadeusz A. Tyndorf, Manalapan;
Susan L. Barker, Tenafly, both of N.J.

[73] Assignee: Becton Dickinson and Company, Franklin Lakes, N.J.

[21] Appl. No.: 820,920

[22] Filed: Mar. 19, 1997

[51] Int. Cl.$^6$ ................................................. C12M 3/00
[52] U.S. Cl. .................................. 435/297.5; 435/305.2; 435/305.3; 435/288.4; 422/102
[58] Field of Search ........................... 435/288.3, 288.4, 435/297.5, 305.1, 305.2, 305.3, 305.4; 422/102

[56] References Cited

U.S. PATENT DOCUMENTS

| | | | |
|---|---|---|---|
| 1,515,016 | 11/1924 | Earp-Thomas | 435/299 |
| 4,657,867 | 4/1987 | Guhl et al. | 435/284 |
| 5,358,871 | 10/1994 | Stevens et al. | 435/284 |
| 5,366,893 | 11/1994 | Stevens et al. | 435/284 |
| 5,417,576 | 5/1995 | Hill | 435/299 |

FOREIGN PATENT DOCUMENTS

2 269 391  2/1994  United Kingdom ............. C12M 1/00

*Primary Examiner*—David A. Redding
*Attorney, Agent, or Firm*—Bruce S. Weintraub; Nanette S. Thomas

[57] ABSTRACT

A multiwell tissue culture assembly for culturing cells comprising a plate and a lid. The plate includes a plurality of wells for accommodating a cell culture insert and the lid includes means for varying the gas diffusion into and out of the assembly and for substantially minimizing biological contamination of the cells being cultured in the cell culture insert. The means for varying the gas diffusion is a gas permeable membrane provided in a plurality of openings in the lid and a plurality of removable thin impermeable film labels are provided for selectively occluding passage of gases through the gas permeable membranes.

17 Claims, 6 Drawing Sheets

FIG-3

CULTURE VESSEL ASSEMBLY

BACKGROUND OF THE INVENTION

1. Field of the Invention

This invention relates to an apparatus and procedures for growing cells or tissue culture in vitro and more particularly to a culture vessel assembly having means for varying the gas diffusion rate into and out of the assembly and for substantially minimizing biological contamination of the cells or tissue culture in the assembly.

2. Description of Related Art

Culture vessels are described in U.S. Pat. Nos. 4,495,289, 5,026,649, 5,358,871 and 5,366,893 and European Patent Application No. 0 483 620 A2 and U.K. Patent Application No. GB 2 268 187 A. Culture vessels comprise wells which generally have a circular shape and size which permits the introduction therein of a cell culture insert having a membrane upon which cell attachment, growth and differentiation occur. The culture vessels containing the wells are typically rectangular and have a standard size in order to accommodate standard analytical apparatus. Cell culture inserts used in culture vessels are described in U.S. Pat. Nos. 4,871,674, 5,026,649 and 5,366,893 and are herein incorporated by reference.

The culture of cells is dependent upon the ability to supply sufficient oxygen to the cells without causing cellular damage. The supply of oxygen for cell respiration is from the atmosphere in the header space above the cells via the liquid culture medium.

Aeration of the culture, by for example, sparging, surface aeration, medium perfusion, can increase the oxygen availability, however such methods can cause cellular damage. Silicone rubber tubing has been used to improve gas exchange in cell culture, by running the tubing between the well and the atmosphere but this method is inconvenient and may cause contamination to the cell suspension.

Although there are a number of culture vessels commercially available and described in patent publications, it is believed that there are no culture vessels available that provide a means for varying the gas diffusion rate into and out of a culture vessel assembly while still providing a closed system whereby entry or exit of biological contaminants into or out of the vessel is substantially minimized.

SUMMARY OF THE INVENTION

The present invention is an assembly for growing cells or tissue culture in vitro. The assembly comprises a test plate with wells shaped to accommodate an insert, such as a cell culture insert or for receiving tissue culture media, and a removable lid.

The test plate preferably comprises an upper surface, a lower surface, and a plurality of wells. Each well is substantially disposed between the upper and lower surface of the test plate.

The assembly further includes a removable lid which can be positioned over the upper surface of the test plate. The lid includes a top wall and a peripheral skirt that extends downwardly from the top wall. The lid serves to prevent the loss of sample from the well interior, to protect the contents of the assembly from the environment and to protect the user from the contents of the assembly should it contain a harmful or potentially harmful material.

The test plate and related removable lid may be formed in different sizes and geometric configurations so as to be used with different size and geometric configured cell culture inserts. The removable lid may be formed to be positioned over the upper surface of the plate in one orientation so as to reduce cross contamination between the wells in the event the lid is repositioned over the upper surface of the plate. The plate and the removable lid are preferably made of an optically clear plastic to facilitate viewing of the wells and cell culture inserts.

Preferably, the lid comprises means for allowing gas diffusion into and out of the wells of the plate. Most desirably, the means for allowing the gas diffusion into and out of the wells of the plate is at least one port and associated with the port is a gas permeable membrane. Most preferably, the gas permeable membrane is liquid impermeable. Most preferably, the lid comprises the same number of ports as there are wells in the companion plate. In addition, most preferably, the ports are positioned or aligned with the wells. Therefore, when the lid is placed over the plate, each well is associated with a port on the lid. The positioning of the port with the well provides the advantage of improved gas exchange directly with the well. Furthermore, gas exchange can be controlled more directly by well, whereby each well may receive individualized attention for the gas exchange by the user.

Further associated with the lid is a means for selectively occluding the gas permeable membrane without removing the lid from the test plate. Preferably, the means for selectively occluding the membrane is a thin impermeable film. A thin film may be removably attached to the top of the lid over each individual port to restrict exposure of the gas permeable membrane to the atmosphere. The thin impermeable film assists is maintaining the biological security of the environment in the wells because the lid does not have to be lifted or removed from the test plate.

Most preferably, the means for selectively occluding the membrane is a peel-away gas impermeable label. Most preferably, the label is plastic. Preferred materials of the label, include but are not limited to polymeric substrate resins that are impermeable to gases and liquids. The label may be transparent or color coded. Moreover, the surface of the label may be such that additional information may be hand written on the label.

Although it is within the purview of the invention to provide a label that is circular, labels of different geometric configurations may be provided.

The label allows the user to control the exchange of gas in the test plate so that the desired growth of the cell culture can be facilitated in the test plate while still providing a closed system that substantially prevents entry of microbial organisms or other contaminants into the wells of the test plate. The label substantially maximizes gas exchange while minimizing the possibility of contamination in the wells of the test plate. A further advantage is that gas exchange takes place exclusively through the membrane without having to remove or partially open the lid.

The label does not compromise sterility or invite leakage into the test plate. Other advantages is that the label is reusable and is economically feasible to manufacture.

Most notably, the assembly of the present invention provides the following advantages: (1) a closed vented environment while maintaining sterility and controlling gas exchange; (2) containment of potentially hazardous samples; and (3) minimizing contamination of specimen in the assembly with environmental/exogenous contaminants such as yeast, bacteria and/or virus.

In addition, the assembly of the present invention is particularly advantageous when culturing layers of cells, such as in skin cultures where it is desirable to produce layers of keratinocytes for skin grafting in a sterile and gas exchange controlled environment In addition, the present invention allows for the controlled passage of oxygen directly to the dividing cells which lie on the membrane surface of the cell insert.

In accordance with the principles of the assembly of the present invention, significant improvements over currently known and available multiwell tissue culture assemblies are provided. Most importantly, the present invention substantially improves gas diffusion into and out of the assembly while maintaining the sterility of the contents of the multiwell plate and allows adequate gaseous exchange to occur between the wells and the external environment. Accordingly, the assembly of the present invention provides a biologically closed environment so as to optimize conditions for cell culturing procedures whereby entry or exit of biological contaminants, gases and/or liquids is substantially minimized.

DETAILED DESCRIPTION

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
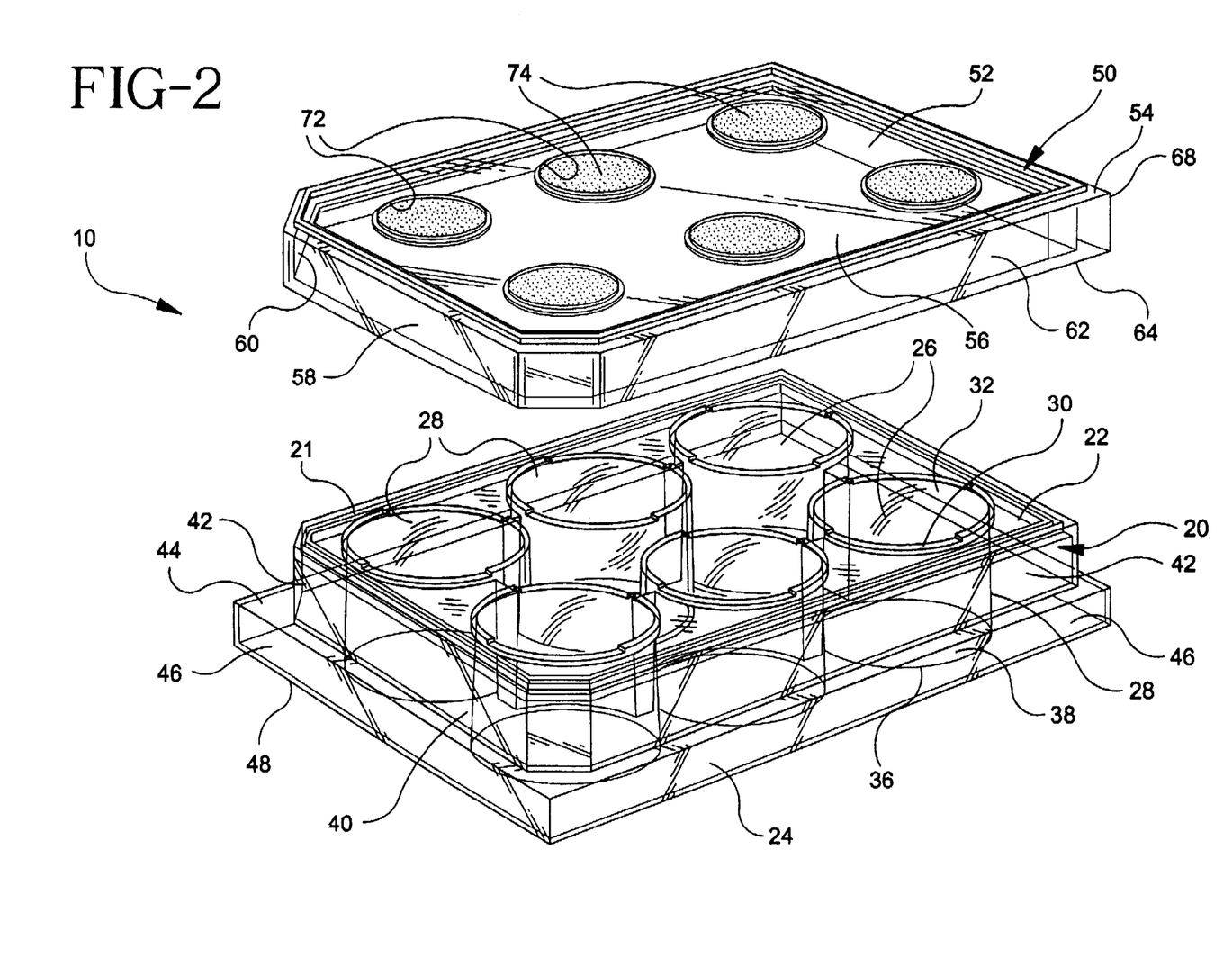
FIG. 2 is a perspective view of the assembly of the present invention with the lid removed.
Figure 3:
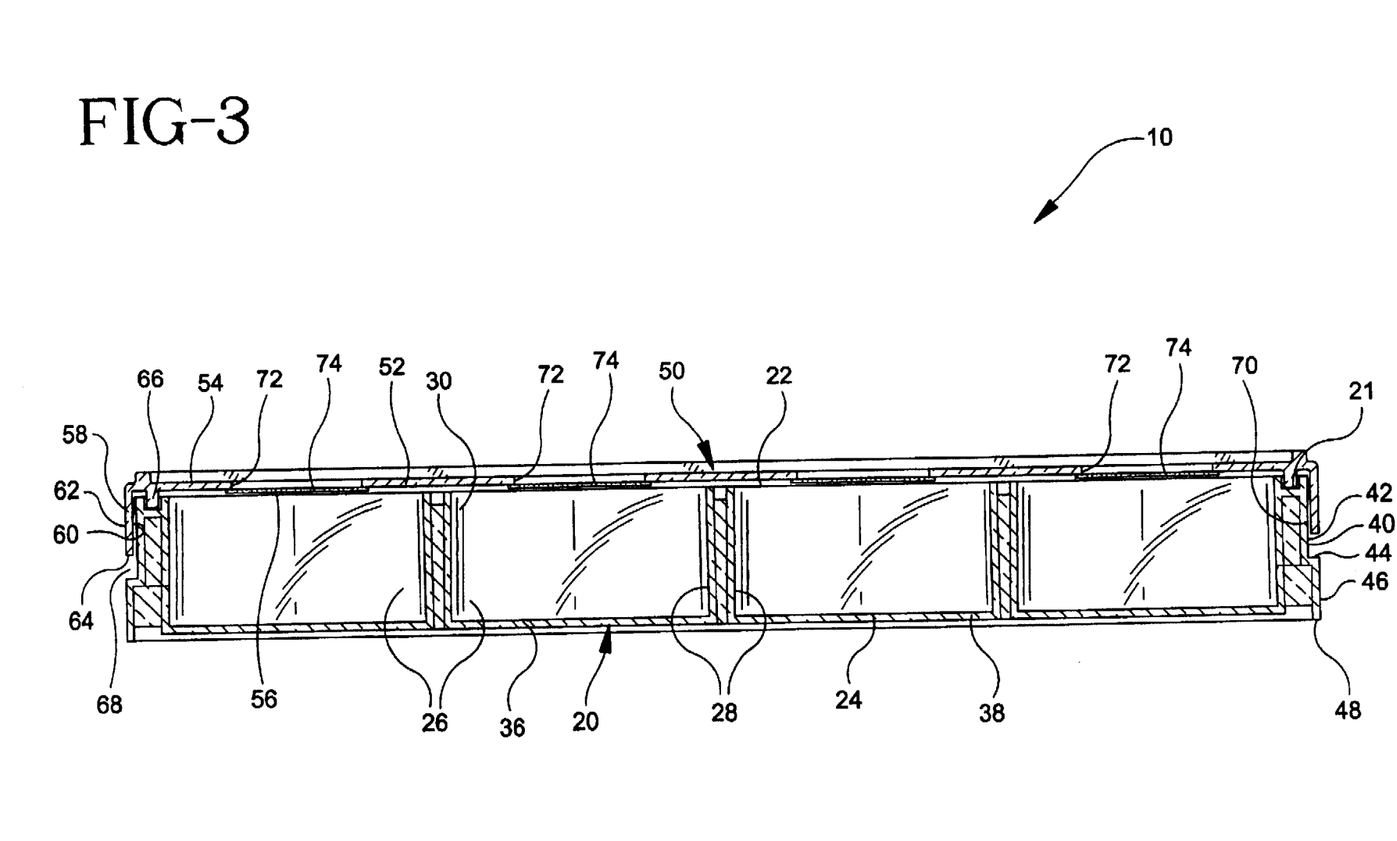
FIG. 3 is a cross-sectional view of the assembly taken along lines 3—3 of FIG. 1.

An apparatus 10 for growing tissue culture as shown in FIGS. 2–3 includes a culture vessel plate 20 and a lid 50. As shown in FIGS. 2–3 culture vessel plate 20 includes an upper surface 22 and lower surface 24. The culture vessel plate further includes a number of wells 26 each comprising a sidewall 28 extending from upper surface 22 of the plate to lower surface 24 of the plate. Each well comprises a top portion 30 and a bottom portion 36. Top portion 30 comprises an open end 32, that extends to bottom portion 36 that comprises a closed end 38.

Figure 1:
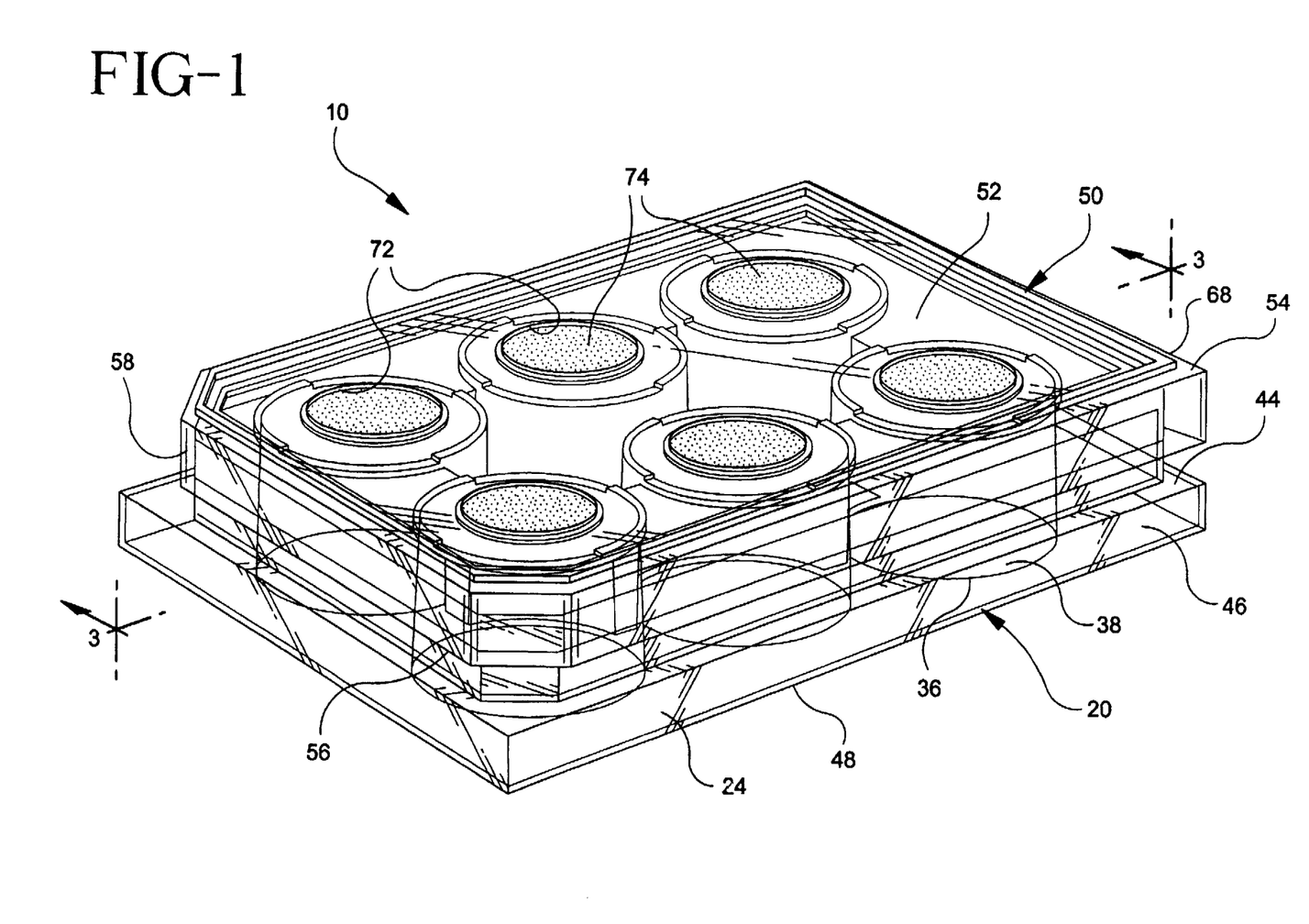
FIG. 1 is a perspective view of the assembly of the present invention.

There may be any number of wells 26 in plate 20, although six, twelve, twenty-four, forty-eight and ninety-six well plates are commonly known and available. In FIG. 1, a six-well plate is illustrated, merely for exemplary purposes. Most standard multiwell plates have the wells arranged in orthogonal rows and columns so as to be able to clearly identify the individual wells being used, of course, the arrangement of the wells in plate 20 is not an essential limitation of the present invention, since any arrangement of wells is contemplated by the invention.

Plate 20, as illustrated in the figures, typically is transparent and may be molded, for example, of polyvinylchloride or polystyrene.

Surrounding the wells and forming the outside border of plate 20 is sidewall 40. In the present embodiment, plate 20 has six (6) sidewalls. Well known tissue culture plates are rectangle or quadrilaterally shaped, although for purposes of the present invention the plate may be fabricated in any practical configuration and contain any number of wells.

Spaced inwardly from sidewalls 40 and around the upper surface of plate 20 is a recessed ledge 21 as more clearly seen in FIGS. 2 and 3. Ledge 21 forms a border around the wells on the upper surface 22 of plate 20 and wherein the sidewalls 40 extend to a position raised above the ledge thereby forming a rim surrounding the ledge.

Sidewall 40 comprises a two-step section comprising an upper section 42 and a lower section 46. Lower section 46 is stepped from upper section 42 by an annular shoulder 44 between the upper and lower sections. Therefore, upper section 42 extends from the upper surface 22 to an annular shoulder 44 and lower section 46 extends from annular shoulder 44 to bottom surface 48 of lower surface 24.

Lower section 46 serves as an annular base for plate 20 when the present multiwell tissue culture apparatus is being used.

Figure 4:
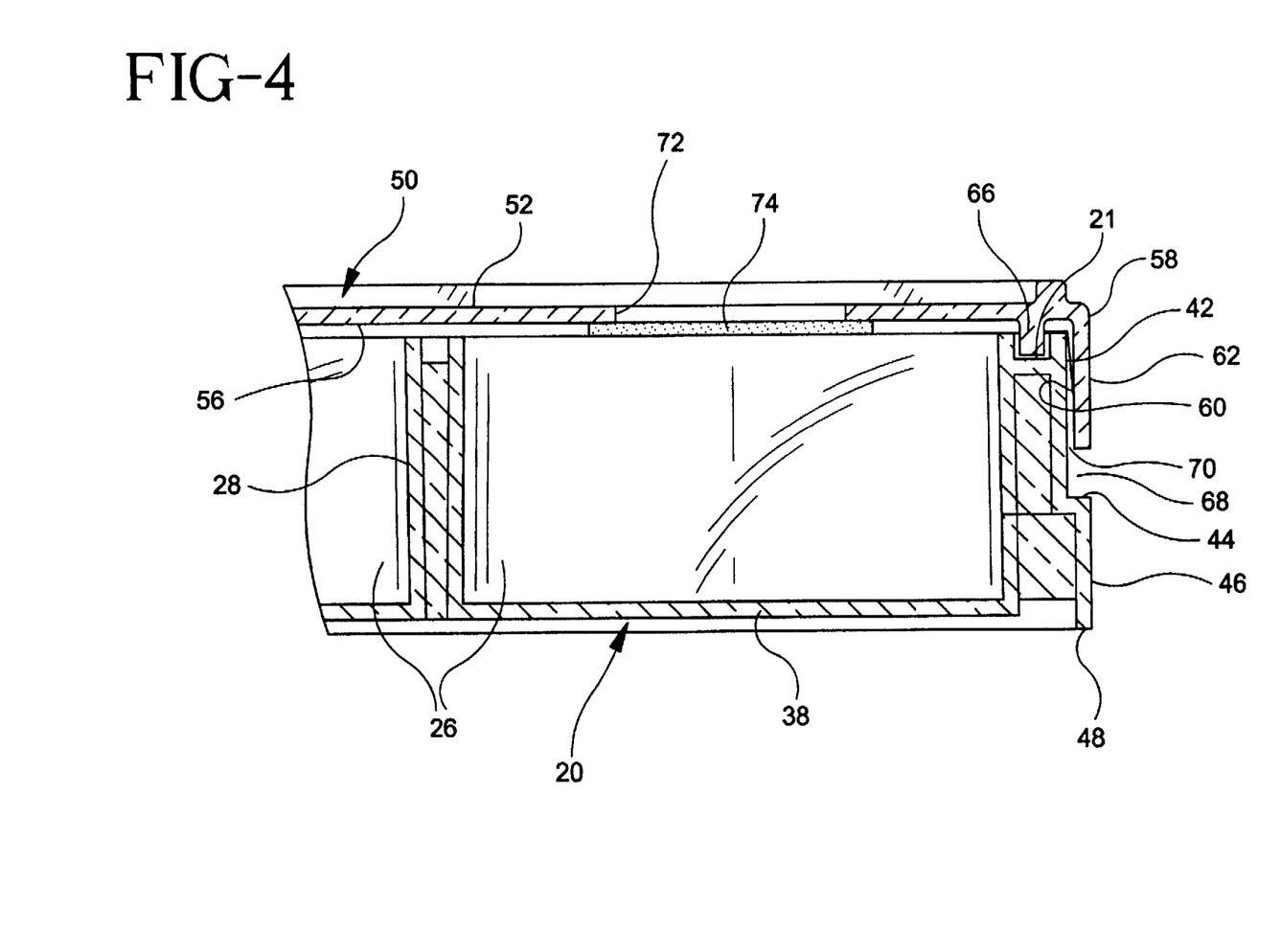
FIG. 4 is an enlarged, partial sectional view of the assembly of FIG. 3.

Lid 50 is a separate, removable member which covers all of the wells of the plate. Although lid 50 is illustrated in all of the figures, the details of lid 50 are best illustrated in FIGS. 3–4. Lid 50 includes a substantially planar cover 52 large enough to extend over all of the wells of the plate. Planar cover 52 has a top surface 54 and a bottom surface 56. The shape of cover 52 is compatible with the shape of plate 20. Most preferably, as shown in FIG. 1, lid 50 is formed to be positioned over the upper surface of the plate in one orientation so as to reduce cross contamination between the wells in the event the user tries to reposition the lid over the plate.

Extending around cover 52 is a downwardly depending skirt 58 which forms a border around lid 50. Skirt 58 has an inner wall surface 60 and an outer wall surface 62, and six sides each of which extends downwardly from the cover to a bottom stop surface 64. Inwardly, spaced from skirt 58 and extending downwardly from bottom surface 56 of the planar cover is rib 66. This rib, lying substantially parallel to each of the sides of skirt 58 is positioned on the cover so as to depend downwardly into recessed ledge 21 in the plate.

As shown in FIG. 4, when lid 50 is positioned over plate 20, skirt 58 extends towards annular shoulder 44 of the plate thereby leaving a space 68 therebetween annular shoulder 44 and bottom stop surface 64. Moreover, as shown in FIG. 4, there is a second space 70 between inner wall surface 60 of skirt 58 and upper section 42 of the sidewall of the plate.

Located on cover 52 is a number of orifices 72 as shown in FIGS. 1–3. A gas permeable, liquid impermeable membrane 74 is associated with each orifice as shown in FIGS. 1–3. The orifices and associated membranes are arranged on the cover so that when the cover is positioned over the plate, an orifice and membrane is associated with each individual well in the plate.

Gas permeable membrane materials may be made from any suitable gas permeable material so long as it provides free passage of gases such as oxygen and carbon dioxide into the test plate while preventing microorganisms such as bacteria and fungi from passing there through. These materials include polyethylene, polycarbonate, acrylic co-polymers and polytetrafluoroethylene.

Figure 5:
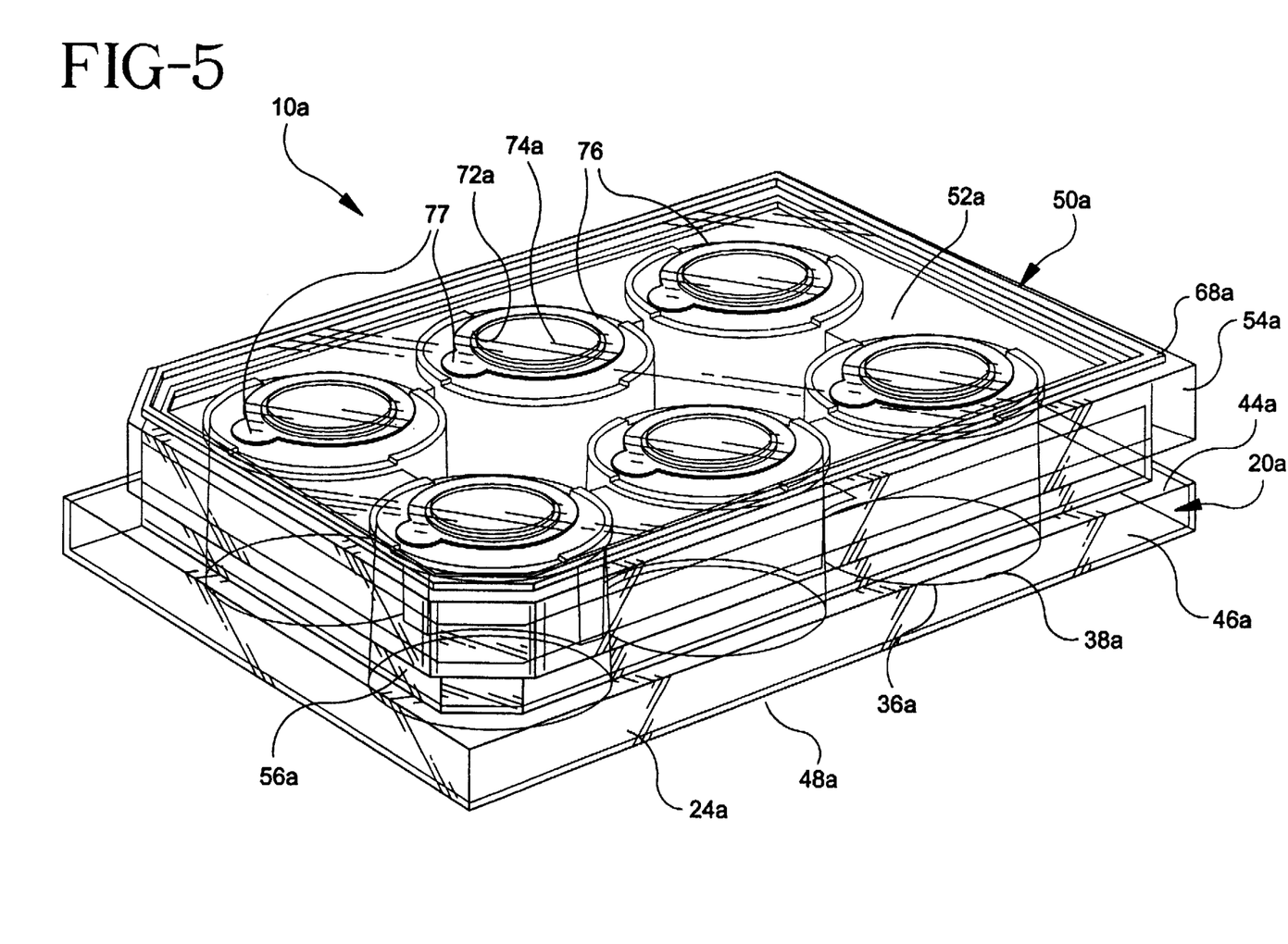
FIG. 5 is a perspective view of an alternate embodiment of the present invention with a label covering each orifice.

An additional embodiment of the invention as shown in FIG. 5 includes many components which are substantially identical to the components of FIG. 1. Accordingly, similar components performing similar functions will be numbered identically to those components of FIG. 1 except that a suffix "a" will be used to identify those similar components in FIG. 5.

As shown in FIG. 5, optional peel-away thin film labels 76 are removably attached to cover 52a to selectively occlude membranes 74a of orifices 72a. The films may be fully or partially removed or left in place according to the particular culture requirements.

Conventional means are used to apply the peel-away thin film label to the cover. These means include adhesive materials such as pressure sensitive materials, wherein the thin film label can be easily fully or partially removed from the cover as is required and reapplied as needed. The thin film label material may be made of polyethylene or polyethylene terephthalate and adhesive materials may include acrylic adhesives.

As shown in FIG. 5, each peel-away thin film label 76 is circular and has a tab 77 for ease of use. Although it is within the purview of the invention to provide a peel-away thin film that is circular, films of different geometries and dimensions may be provided.

Figure 6:
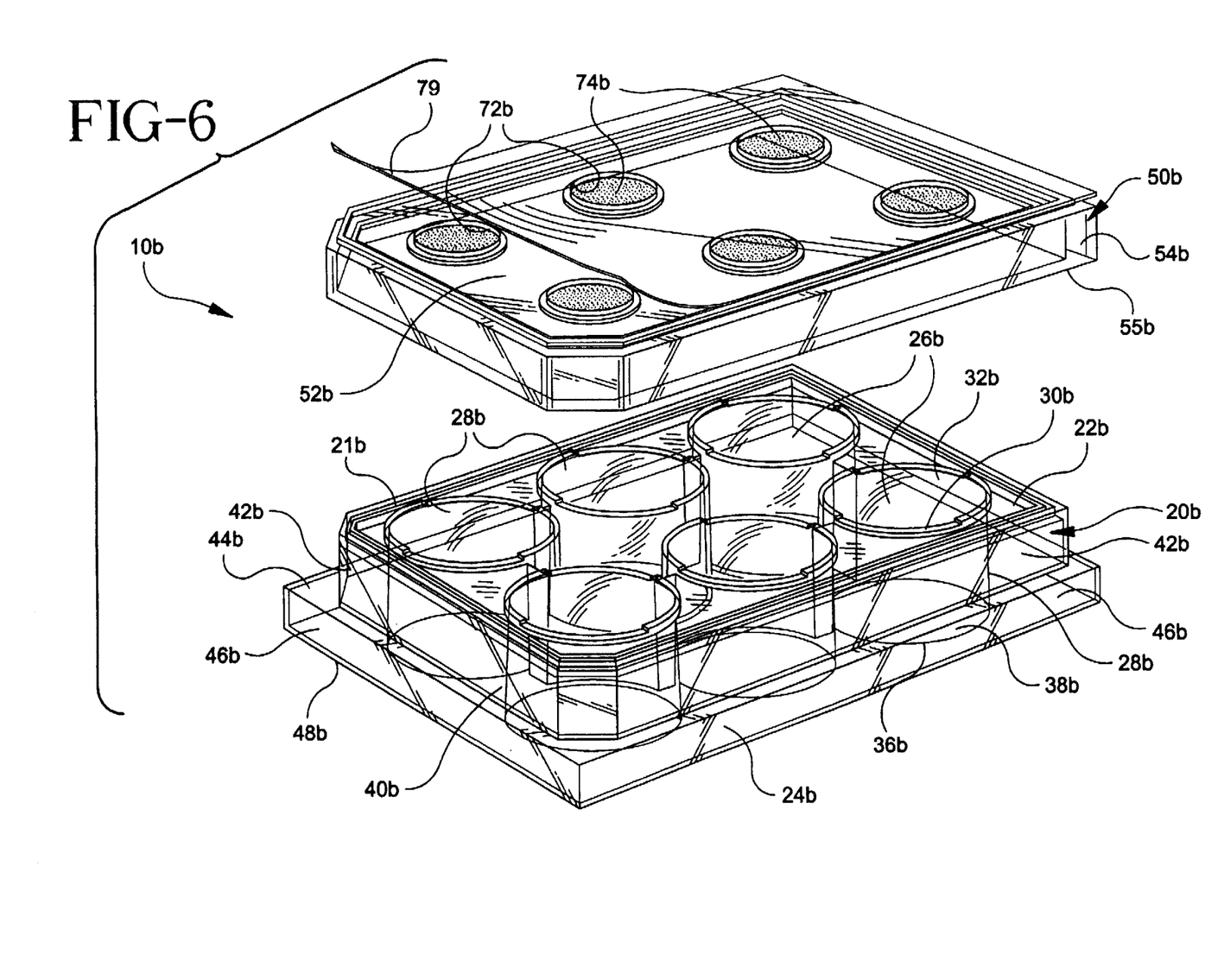
FIG. 6 is a perspective view of an alternate embodiment of the present invention with a label covering the entire lid.

An additional embodiment of the invention as shown in FIG. 6 includes many components which are substantially identical to the components of FIG. 2. Accordingly, similar components performing similar functions will be numbered identically to those components of FIG. 2, except that a suffix "b" will be used to identify those similar components in FIG. 6.

Label 79 as shown in FIG. 6 is an alternate embodiment of the label that can be used with assembly 10b. The alternate embodiment of the invention as shown in FIG. 6, is that label 79 covers the entire planar cover surface of lid 50b.

In use, the present invention may be used for culturing cells as follows:

a. removing the lid from the culture vessel assembly;
b. depositing a layer of cells on the membrane of the cell insert within the culture vessel;
c. overlaying the layer of cells with a growth medium;
d. placing the lid over the vessel; and
e. directly ventilating the membrane of each cell insert by permitting air access thrusts through the orifices in the lid of the culture vessel by removing or partially removing and re-attaching the labels over the orifices.

As practitioners-in-the-art will understand, the culture vessel assembly of the present invention may be comprised of simple moldable parts which may be mass produced from a variety of materials, including, for example, polyethylene, polystyrene, polyethylene terephthalate and polypropylene. As will be understood further by practitioners in the art, materials should be selected which provide a small degree of resiliency for the purpose of providing ease of use for subsequent examination of the developed cultured cells.

What is claimed is:

1. An assembly comprising:
   a test plate comprising a plurality of wells having openings therein for receiving tissue culture media or cell culture inserts and upstanding sidewall forming an outside border of said plate;
   a lid removably positioned on said plate comprising a substantially planar cover extending over said wells, comprising an upper surface and a lower surface, a skirt surrounding said cover defining a plurality of corners on said cover and extending downwardly in spaced relation with respect to said sidewall of said plate, to form sidewalls having an inner and outer surface; and
   a plurality of orifices in said planar cover each comprising a gas permeable membrane and positioned whereby said orifices are in alignment with said wells of said test plate.

2. The assembly of claim 1 further comprising gas impermeable films removably attached to said cover and associated with each orifice whereby said film may be fully or partially removed to assist in gas diffusion into and out of said assembly.

3. The assembly of claim 1 wherein said sidewall of said plate comprises a two-step section comprising an upper section and a lower section.

4. The assembly of claim 3 wherein said lower section of said sidewall is stepped from said upper section by an annular shoulder.

5. The assembly of claim 1 wherein said skirt of said lid extends to a position adjacent to, but out of contact with, said annular shoulder of said plate.

6. The assembly of claim 1 wherein said wells are arranged in substantially orthogonal rows and columns.

7. The assembly of claim 1 wherein said plate and said lid are made of transparent plastic.

8. The assembly of claim 1 wherein said test plate further comprises a ledge spaced inwardly from said sidewall of said plate and extending between said sidewalls and said wells wherein said sidewalls extend to a position raised above said ledge thereby forming a rim surrounding said ledge.

9. A lid for use in conjunction with a tissue culture plate comprising:
   a substantially planar cover comprising an upper surface and a lower surface;
   a skirt surrounding said cover defining a plurality of corners on said cover and extending downwardly to form sidewalls having an inner and outer surface;
   a plurality of orifices in said cover each comprising a gas permeable membrane; and
   gas impermeable films removably attached to said cover over each of said orifices and said gas permeable membranes whereby each film may be fully or partially removed.

10. The lid of claim 9 wherein said gas impermeable films are peel-away labels.

11. The lid of claim 10 further comprising a plurality of flanges being inwardly spaced from said skirt and extending downwardly from said lower surface of said cover.

12. A device for growing cells or tissue culture in vitro comprising:
   a body comprising an upper surface, a lower surface, a plurality of wells substantially disposed between said upper and lower surface and upstanding sidewall forming an outside border of said body; and
   a removable lid, comprising a top wall and a peripheral skirt that extends from said top wall and a plurality of means for allowing gas diffusion into and out of said device at said top wall, wherein said plurality of means is in alignment with said wells of said body.

13. The device of claim 12 wherein said plurality of means for allowing gas diffusion into and out of the device is a plurality of orifices and gas impermeable membranes associated with said orifices and in direct alignment with said wells of said body.

14. The device of claim 13 further comprising a plurality of gas impermeable films removably attached to said cover over said orifices, whereby said films may be fully or partially removed to assist with gas diffusion in said device.

15. The device of claim 12 wherein said sidewall of said body includes a two step section comprising an upper section and a lower section.

16. The device of claim 15 wherein said sidewall of said body further comprises an annular shoulder whereby said lower section is stepped from said upper section by said annular shoulder.

17. A method of culturing cells comprising:

(a) providing a culture vessel comprising a test plate comprising a plurality of wells having openings therein for receiving tissue culture media and upstanding sidewall forming an outside border of said plate; a lid removably positioned on said plate comprising a substantially planar cover extending over said wells, a skirt surrounding said cover defining a plurality of corners on said cover and extending downwardly to form sidewalls having an inner and outer surface; a plurality of orifices in said planar cover each comprising a gas permeable membrane wherein said orifices are in direct alignment with said wells of said plate; and removable labels associated with said orifices to cover said membrane;

(b) removing said lid from said culture vessel;

(c) placing cell inserts comprising a membrane within said wells of said culture vessel;

(d) depositing a layer of cells on each membrane of said cell insert within said culture vessel;

(e) overlaying the layer of cells with a growth medium;

(f) placing said lid on said plate to cover said wells; and (g) directly ventilating said membrane of each cell insert by permitting air access thrusts through said orifices in said lid of said culture vessel by fully or partially removing and re-attaching said labels over said orifices.

* * * * *